US006310831B1

(12) United States Patent
Dillman

(10) Patent No.: US 6,310,831 B1
(45) Date of Patent: Oct. 30, 2001

(54) METHOD AND SYSTEM FOR APERTURE ADJUSTMENT IN STEERED PHASED ARRAY TRANSDUCER SYSTEMS

(76) Inventor: Richard F Dillman, 278 High Plain Rd., Andover, MA (US) 01810

( * ) Notice: Subject to any disclaimer, the term of this patent is extended or adjusted under 35 U.S.C. 154(b) by 0 days.

(21) Appl. No.: 09/504,533

(22) Filed: Feb. 15, 2000

(51) Int. Cl.[7] .................................................. G01S 15/00
(52) U.S. Cl. .............................................. 367/105; 367/103
(58) Field of Search ................................... 367/7, 103, 105; 73/625, 626; 600/443, 444

(56) References Cited

U.S. PATENT DOCUMENTS 4,058,003 * 11/1977 Macovski ............................... 73/609
4,180,790 * 12/1979 Thomas et al. ........................ 367/7
4,180,791 * 12/1979 Tiemann ............................... 367/205

OTHER PUBLICATIONS

Lockwood et al., "Optimizing the Radiation Pattern of Sparse Periodic Two–Dimensional Arrays," IEEE Transactions on Ultrasonics, Ferroelectrics and Frequency Control, vol. 43, No. 1, Jan. 1996.*

Lockwood et al., "Optimizing Sparse Two–Dimensional Transducer Arrays using an effective aperture approach," Ultrasonics Symposium, 1994 Proceedings.*

* cited by examiner

Primary Examiner—Ian J. Lobo

(57) ABSTRACT

A method and system for compensating for steering anomalies by adjusting aperture in steered phased array transducer systems adjusts the aperture of a transducer array to effectively compensate for the steering anomalies. The aperture of the transducer array can be varied depending upon the steering angle of the beam and the resultant steering angle anomalies.

18 Claims, 7 Drawing Sheets

METHOD AND SYSTEM FOR APERTURE ADJUSTMENT IN STEERED PHASED ARRAY TRANSDUCER SYSTEMS

TECHNICAL FIELD

The present invention relates generally to ultrasonic transducers, and, more particularly, to a method and system for compensating for steering anomalies by adjusting aperture in steered phased array transducer systems.

BACKGROUND OF THE INVENTION

Ultrasonic transducers have been available for quite some time and are useful for interrogating solids, liquids and gasses. One particular use for ultrasonic transducers has been in the area of medical imaging. Ultrasonic transducers can be fabricated from piezoelectric materials or can be a new form of ultrasonic transducer known as a micromachined ultrasonic transducer (MUT). Piezoelectric transducer elements typically are made of material such as lead zirconate titanate (abbreviated as PZT), with a plurality of elements being arranged to form a transducer assembly. MUT's are typically fabricated using semiconductor manufacturing techniques with a number of elements typically formed on a common substrate to form a transducer assembly. Regardless of the type of transducer element, the transducer assembly is then further assembled into a housing possibly including control electronics, in the form of electronic circuit boards, the combination of which forms an ultrasonic probe. This ultrasonic probe, which may include acoustic matching layers between the surface of the PZT transducer element or elements and the probe body, may then be used to send and receive ultrasonic signals through body tissue.

Typically, the transducer elements within the ultrasonic probe are excited by a voltage signal, which causes each transducer element to emit an interrogation pulse, or beam. It is possible to control the application of the voltage signal to each transducer element within the array through the use of delay circuitry associated with each transducer element and thereby direct the resulting beam. After interrogating the target, the pulse is reflected back to the ultrasonic probe where the transducer elements, operating in a receive mode, receive the ultrasonic energy, convert the ultrasonic energy to electrical signals, and pass the electrical signals to receive circuitry. The receive circuitry analyzes the received energy and constructs an image for presentation to a viewer.

Oftentimes, it is desirable to steer and focus the ultrasonic energy transmitted to a target and received from the target. To steer and focus the beam on transmit, the transmit delays are adjusted to equalize the time for a pulse to propagate to the desired focal point in the image plane substantially perpendicular to the transducer elements at a defined distance from the center of the surface of the transducer array and at a defined angle to a line normal to the surface of the transducer array.

To steer and focus the beam on receive, the receive delays are adjusted to equalize the time for a pulse to propagate from the desired focal point. For both transmit and receive, a contiguous subset, or aperture, of the available transducer elements are enabled. A larger aperture results in a narrower beam and reduced depth of field. Often the transmit aperture is smaller than the receive aperture since dynamic receive focusing (fine adjustment of the receive delays as the wave front moves deeper) makes depth of field a greater concern on transmit than receive.

To display an image, control circuitry causes the transducer elements to pulse repeatedly using different transmit and receive delay settings to achieve different angles. As this is done the properties of the ultrasound beam change subtly. Looking directly forward with respect to the probe, both the transmit and the receive beams typically have higher amplitude, are narrower, and have less depth of field than they do at off-angles. The term "off-angles" refers to angles formed by the transmit or receive of a beam that is steered to angles other than substantially perpendicular to the plane of the transducer element.

Unfortunately, the effect of larger off-angles typically provides a beam having reduced power and reduced resolution, resulting in a weaker image at off-angles. One manner of improving image uniformity at off-angles is to increase transmitter voltage and/or receive amplifier gain at off-angles. Note, however that beam width and depth of field may remain uncorrected. Also, when gain is increased, the system's sensitivity to thermal noise is also increased resulting in more noise in the image at off-angles.

The above discussion assumes linear effects. Increasingly, non-linear effects such as the bursting of contrast bubbles or the generation of harmonics by bubbles or tissues are being exploited by ultrasound systems. Images based on non-linear effects are even more vulnerable to non-uniformities due to transmit amplitude than images based on linear effects. For example, received second harmonic signals can be expected to decrease by two dB for each reduction of one dB in transmit amplitude. This particular problem can be addressed by increasing transmit voltage at the off-angles. However, this requires a difficult and expensive power supply to accomplish and leaves other transmit beam issues than amplitude as well as all receive beam issues not addressed.

Therefore, it would be desirable for a steered beam emanating from and received by an ultrasonic transducer array to exhibit uniform characteristics at all angles.

SUMMARY OF THE INVENTION

The invention provides a method and system for compensating for the undesirable effects of steering an ultrasonic transmit beam.

The present invention may be conceptualized as a method for adjusting a transducer transmit aperture to compensate for transducer steering angle anomalies, comprising the steps of: applying an excitation signal to selected transducer elements in a transducer array, each of the selected transducer elements excited at a time relative to the time of excitation of the other selected transducer elements, resulting in a steered ultrasonic beam, and changing the angle of the steered ultrasonic beam by varying the relative excitation times of each of the selected transducer elements, thereby causing steering angle anomalies. The method also includes the step of compensating for the steering angle anomalies by applying the excitation signal to different transducer elements.

The invention may also be conceptualized as a method for adjusting transducer receive aperture to compensate for transducer steering angle anomalies, the method comprising the steps of: receiving acoustic energy in selected transducer elements, and converting, in each of the selected transducer elements, the received acoustic energy into an electrical signal corresponding to the acoustic energy received by each of the selected transducer elements. The method also includes the steps of delaying each electrical signal by a time relative to each other electrical signal, summing the received electrical signals corresponding to each of the selected transducer elements resulting in a steered receive sensitivity, changing an angle of the steered sensitivity by varying the delay of each electrical signal relative to the delay of each other electrical signal, thereby causing steering angle anomalies, and compensating for the steering angle anomalies by summing the received electrical signals corresponding to different transducer elements.

The invention may also be conceptualized as a system for adjusting a transducer transmit aperture to compensate for transducer steering angle anomalies, comprising a transducer array including transducer elements, an excitation signal that is applied to selected transducer elements, each of the selected transducer elements excited at a time relative to the time of excitation of each other selected transducer elements. The excitation signal results in a steered ultrasonic beam. The system also comprises a plurality of delay elements configured to change the angle of the steered ultrasonic beam by varying the relative excitation times of each of the selected transducer elements, thereby causing steering angle anomalies, and a plurality of switches associated with the delay elements, the plurality of switches configured to compensate for steering angle anomalies by applying the excitation signal to different selected transducer elements.

BRIEF DESCRIPTION OF THE DRAWINGS

The present invention, as defined in the claims, can be better understood with reference to the following drawings. The components within the drawings are not necessarily to scale relative to each other, emphasis instead being placed upon clearly illustrating the principles of the present invention.

DETAILED DESCRIPTION OF THE PREFERRED EMBODIMENT

Figure 1A:
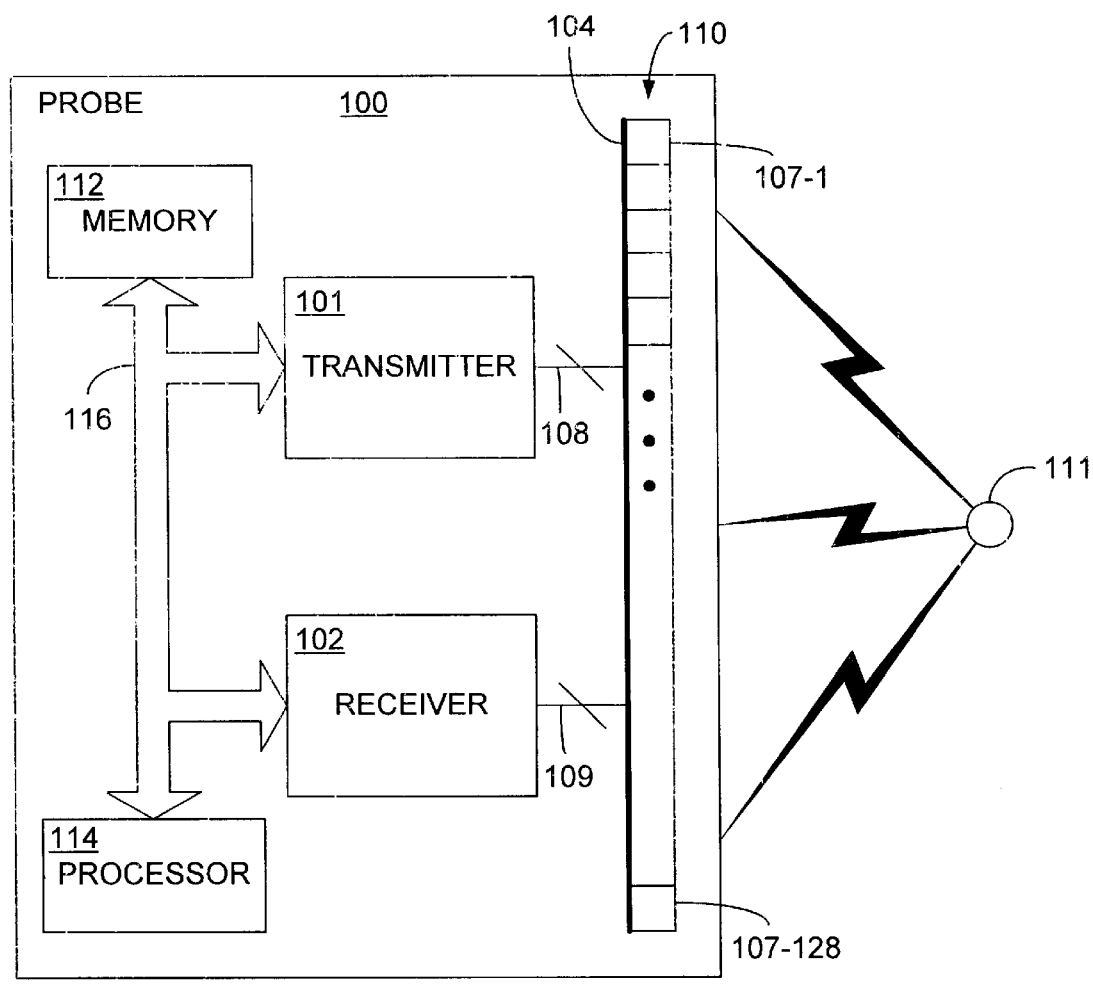
FIG. 1A is a schematic view illustrating an ultrasonic transducer probe.

The invention to be described hereafter is applicable to all ultrasonic transducer arrays that employ beam steering. Furthermore, the concepts of the invention are applicable at various interrogation and receive frequencies and bandwidths.

Furthermore, the method and system for compensating for steering anomalies by adjusting aperture in steered phased array transducer systems of the present invention can be implemented in software, hardware, or a combination thereof. In a preferred embodiment(s), the method and system for compensating for steering anomalies by adjusting aperture in steered phased array transducer systems is implemented in software or firmware that is stored in a memory and that is executed by a suitable instruction execution system (microprocessor). If implemented in hardware, as in an alternative embodiment, the method and system for compensating for steering anomalies by adjusting aperture in steered phased array transducer systems can be implemented with any or a combination of the following technologies, which are all well known in the art: a discrete logic circuit(s) having logic gates for implementing logic functions upon data signals, an application specific integrated circuit having appropriate logic gates, a programmable gate array(s) (PGA), a field programmable gate array (FPGA), etc.

Furthermore, the method and system for compensating for steering anomalies by adjusting aperture in steered phased array transducer systems software, which comprise an ordered listing of executable instructions for implementing logical functions, can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

Furthermore, for simplicity in the description to follow, only the principal elements of the ultrasonic transducer array constructed and operated in accordance with the present invention will be illustrated.

Turning now to the drawings, FIG. 1A is a schematic view illustrating an ultrasonic transducer probe 100. Ultrasonic transducer probe 100 includes transducer array 110, which comprises a plurality of transducer elements 107. Illustratively, transducer array 110 is a one-dimensional array comprising 128 individual transducer elements 107-1 through 107-128. Although shown as a one dimensional transducer array 110, the transducer array can also be a two dimensional array. Each transducer element 107 is connected to bus 104. Bus 104 spans the entire transducer array 110 and connects each transducer element 107 of transducer array 110 to ultrasonic transmitter 101 via connection 108 and to ultrasonic receiver 102 via connection 109. Although shown as single connections, connections 108 and 109 are illustratively connected to each transducer element 107-1 through 107-128 via bus 104. Although shown as contained within ultrasonic probe 100, ultrasonic transmitter 101 and ultrasonic receiver 102 may be located outside of ultrasonic probe 100.

Ultrasonic transducer probe 100 also includes processor 114 and memory 112 in communication with ultrasonic transmitter 101 and ultrasonic receiver 102 via bus 116. While illustrated as a single bus, bus 116 may be used to communicate a number of different types of information including, for example, data, control, and address information. When implemented in software, the logic of the invention may reside within memory 112 and execute in processor 114. In this manner, the operation of ultrasonic transmitter 101 and ultrasonic receiver 102 can be controlled by the logic of the invention to be described below. Furthermore, although shown as contained within ultrasonic probe 100, memory 112 and processor 114 may be located outside of ultrasonic probe 100.

During operation, ultrasonic probe 100 transmits an ultrasonic signal to a target 111 and receives acoustic energy back from target 111. As will be described with respect to FIGS. 2, 3 and 4, during each transmit and receive event, a selected portion of the transducer elements 107 within transducer array 110 will be active at any time. For example, of the 128 transducer elements 107, only 64 transducer elements 107 might be active during any given transmit event. This grouping of 64 transducer elements 107 is known as an aperture of transducer array 110. Similarly, a selected portion of transducer elements 107 might be active during a receive event. For example 64 of the 128 transducer elements 107 might be active during a receive event. This is called the receive aperture. The selection of active transducer elements 107 during transmit and receive events (i.e., the transmit aperture and the receive aperture) may vary.

Figure 1B:
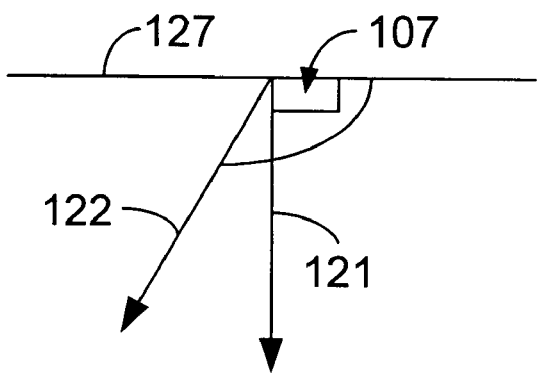
FIG. 1B is a graphical illustration of a substantially perpendicular ultrasonic beam and an off-angle ultrasonic beam generated by a transducer element of FIG. 1A.

FIG. 1B is a graphical illustration of a substantially perpendicular ultrasonic beam and an off-angle ultrasonic beam generated by a transducer element of FIG. 1A. When a substantially perpendicular beam is desired, transducer array 110 (FIG. 1A) is controlled so that the selected transducer elements 107 together emit ultrasonic energy resulting in a beam 121 that is substantially perpendicular to the plane 127 of the transducer 107 (see FIG. 2 below). When an ultrasonic beam is steered (to be described below with respect to FIGS. 3 and 4), the resulting beam of ultrasonic energy resembles off-angle beam 122. Off-angle refers to the angle away from perpendicular with respect to the plane of the transducer elements 107.

Figure 1C:
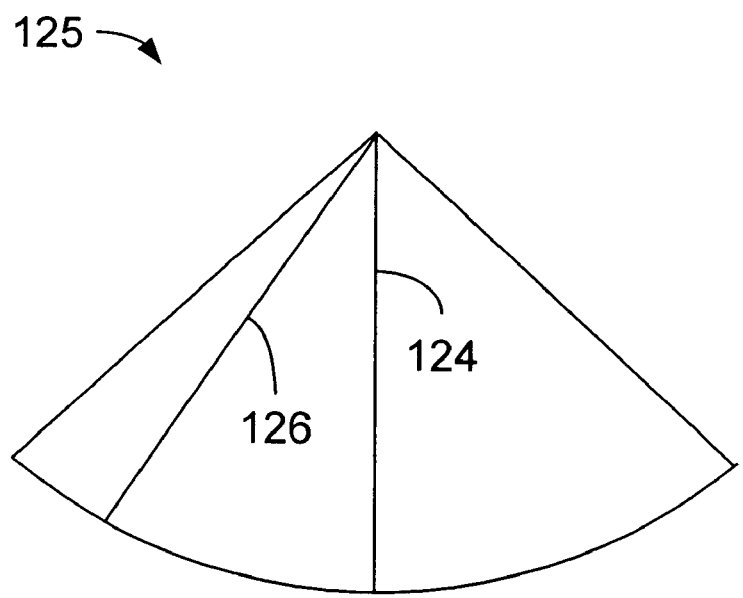
FIG. 1C is a graphical illustration of a sector image generated using the ultrasonic beams of FIG. 1B.

FIG. 1C is a graphical illustration of a sector image 125 generated using the ultrasonic beams of FIG. 1B. In a two dimensional (2D) image, substantially perpendicular line 124 is a representation of the amplitude of echoes received resulting from an ultrasonic transmit beam corresponding to substantially perpendicular beam 121 of FIG. 1B. Similarly, off-angle line 126 is a representation of the amplitude of echoes received resulting from an ultrasonic transmit beam corresponding to off-angle beam 122 of FIG. 1B. In a color image, a line is a representation of the phase shift of echoes received from multiple identical beams.

Figure 2:
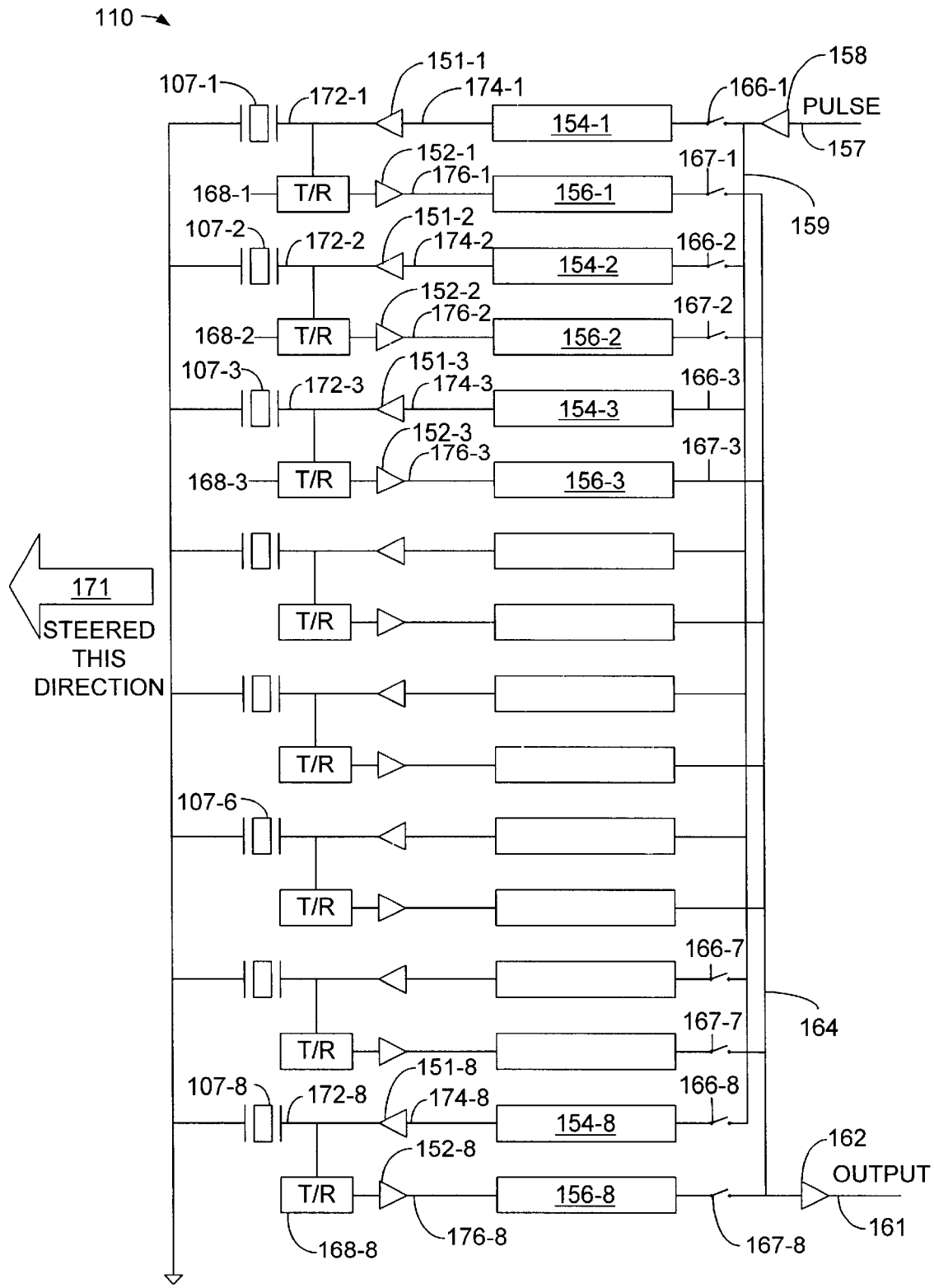
FIG. 2 is a schematic view illustrating the transducer array of FIG. 1A in an unsteered arrangement.

FIG. 2 is a schematic view illustrating transducer array 110 of FIG. 1A in an unsteered arrangement. For simplicity, transducer array 110, as illustrated in FIG. 2, includes eight transducer elements 107-1 through 107-8.

To illustrate a transmit event, an electrical pulse over connection 157 is applied from ultrasonic transmitter 101 (FIG. 1A) to amplifier 158. Depending on the desired aperture, switches 166-1 through 166-8 will either be open or closed, depending on the selection of transducer elements 107-1 through 107-8 that are energized for this transmit event. In the example shown in FIG. 2, switches 166-1 and 166-2 and switches 166-7 and 166-8 are open, therefore the transmit pulse applied from amplifier 158 and onto transmit bus 159 energizes transducer elements 107-3 through 107-6.

Continuing with the description, because switch 166-3 is closed, the transmit pulse on transmit bus 159 is applied through switch 166-3 to transmit delay line 154-3. The transmit pulse is delayed by a predetermined time through transmit delay line 154-3 and is then applied over connection 174-3 to driver 151-3. Driver 151-3 drives transducer element 107-3 via connection 172-3.

During a receive event, transducer element 107-3 receives acoustic energy from target 111 (FIG. 1A). The transducer element 107-3 converts the received acoustic energy (sometimes to referred to as an "echo") to an electrical signal and sends that electrical signal via connection 172-3 through transmit/receive switch 168-3 to receiver 152-3. Receiver 152-3 sends the received signal via connection 176-3 to receive delay line 156-3. Receive delay line 156-3 delays the electrical signal by a predetermined amount of time, that may or may not be equal to the delay time of transmit delay element 154-3, and supplies the signal to switch 167-3, which is closed. The received signal is applied to receive bus 164 for transmission to receive amplifier 162 to be output over connection 161 to ultrasonic receiver 102 (FIG. 1A).

As shown in FIG. 2, the length of each transmit delay line 154-1 through 154-8 and the length of each receive delay line 156-1 through 156-8 is the same. Small differences in the delay elements that are used to focus the beam are not shown. In the transducer element arrangement shown in FIG. 2, the aperture includes transducer elements 107-3 through 107-6. Because switches 166-1, 166-2, 166-7 and 166-8, for transmit events, and switches 167-1, 167-2, 167-7 and 167-8, for receive events, are open, only transducer elements 107-3 through 107-6 receive a transmit pulse from transmit bus 159 and are able to deliver receive signals to receive bus 164. The transducer array 110 shown in FIG. 2 emits and receives ultrasonic energy in the direction indicated by arrow 171 and provides a substantially perpendicular beam. Although shown in FIG. 2 as being steered in the direction indicated by arrow 171, a substantially perpendicular beam is said to be unsteered or steered zero degrees. As will be more fully described with respect to FIGS. 3 and 4, steering of the transmit and receive beams is accomplished by varying the delay lines for each of the transducer elements 107.

Figure 3:
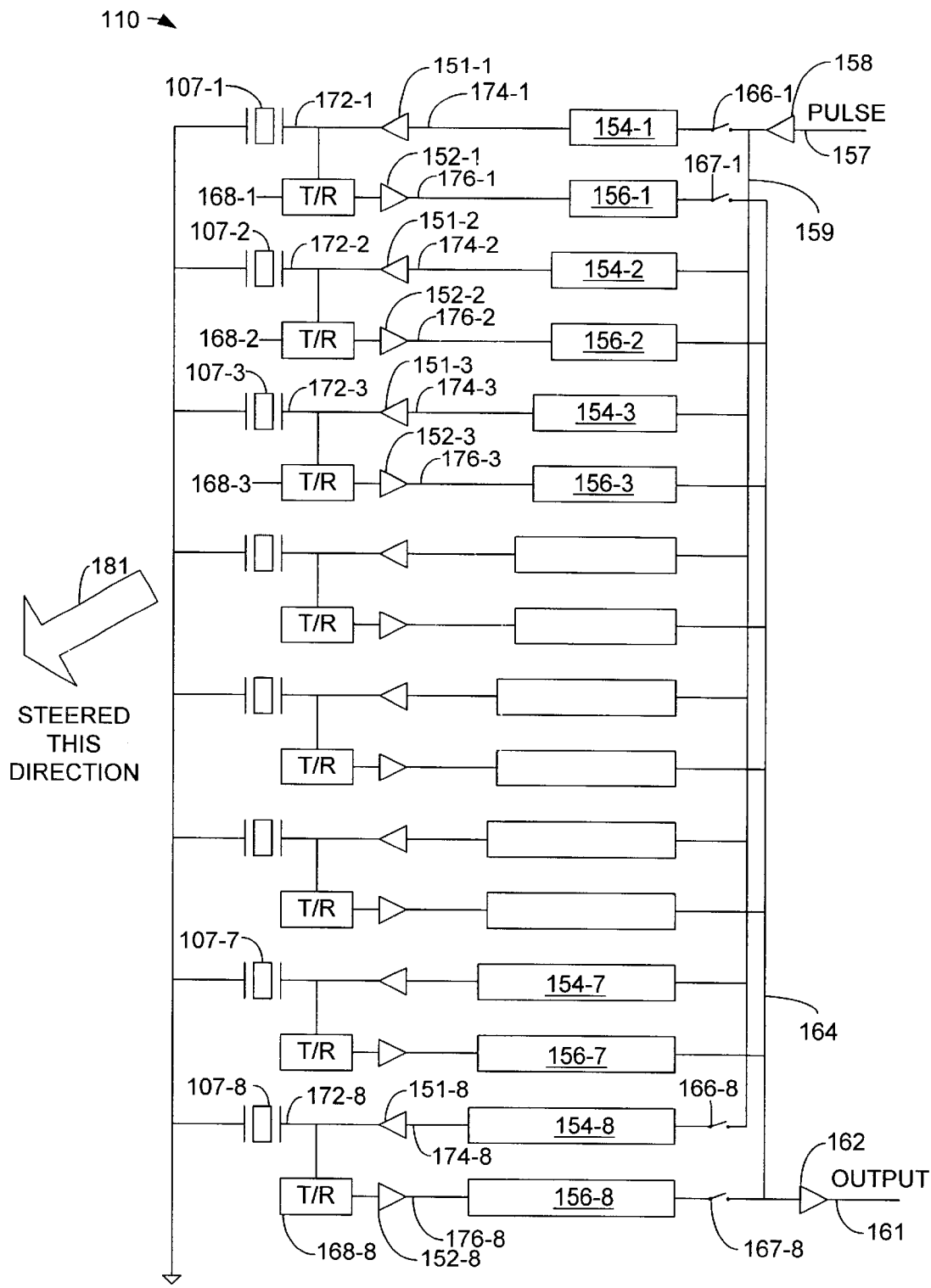
FIG. 3 is a schematic view illustrating transducer array of FIG. 1A in a steered arrangement.

FIG. 3 is a schematic view illustrating transducer array 110 of FIG. 1A in a steered arrangement. As illustrated in FIG. 3, the transmit delay lines 154-1 through 154-8 and the receive delay lines 156-1 through 156-8 are of different duration than that shown with respect to FIG. 2. In this manner, the ultrasonic beam can be steered in the direction indicated by arrow 181. The beam produced by this configuration is considered a non-perpendicular, or off-angle beam as described above.

As shown in FIG. 3, the duration of delay lines 154-2 and 156-2 are shorter than that shown with respect to delay lines 154-7 and 156-7. Indeed, the transmit delay lines 154-1 through 154-8 and the receive delay lines 156-1 through 156-8 are arranged in an increasing order of delay. The increasing order of delay results in the steered beam indicated by arrow 181. As mentioned above, small differences in the delay elements that are used to focus the beam are not shown. Furthermore, as shown in FIG. 3, switches 166-1 and 166-8 for transmit events and switches 167-1 and 167-8 for receive events are the only switches that are open. In this manner, the aperture of transducer array 110 as shown in FIG. 3 includes transducer elements 107-2 through 107-7. It should be noted that in some applications the delay of certain delay elements may be zero.

To develop an ultrasonic image, the transducer array 110 pulses repeatedly using different transmit and receive delay line settings to achieve different angles. As this is done, the properties of the ultrasound beam change subtly causing steering anomalies. When steered substantially perpendicular, as shown in FIG. 2, both the transmit and receive beams typically have higher amplitude, are narrower, and have less depth of field than they would at off-angles. The steering anomalies mentioned above increase as the off-angle increases away from substantially perpendicular. These anomalies typically result in a weaker image at off-angles. To improve image uniformity, this change with angle can be corrected by increasing the aperture on transmit and/or receive at off-angles to compensate for changes in transmit and/or receive beam anomalies such as variations in amplitude, width, and depth of field. In this manner greater image uniformity can be achieved.

As shown in FIG. 3, as the beam is steered in the direction indicated by arrow 181, the aperture has been increased over that shown with respect to FIG. 2 to compensate for the anomalies of the non-perpendicular beam. Specifically, while the aperture shown in FIG. 2 includes transducer elements 107-3 through 107-6, the increased aperture shown in FIG. 3 (i.e., transducer elements 107-2 through 107-7) results in a beam that compensated for the above-mentioned steering anomalies.

In accordance with the invention, variations in both the number of active elements, which controls transmit and receive amplitude, and the extent of active elements, which controls transmit beam width and receive sensitivity width, can be adjusted to compensate for the steering anomalies. One manner in which to determine the degree to which to vary the aperture is to measure the power of the ultrasonic beam at off-angles, and adjust the aperture based upon the power measurements. This method may prove to be desirable as it will handle a wide variety of systems.

Figure 4:
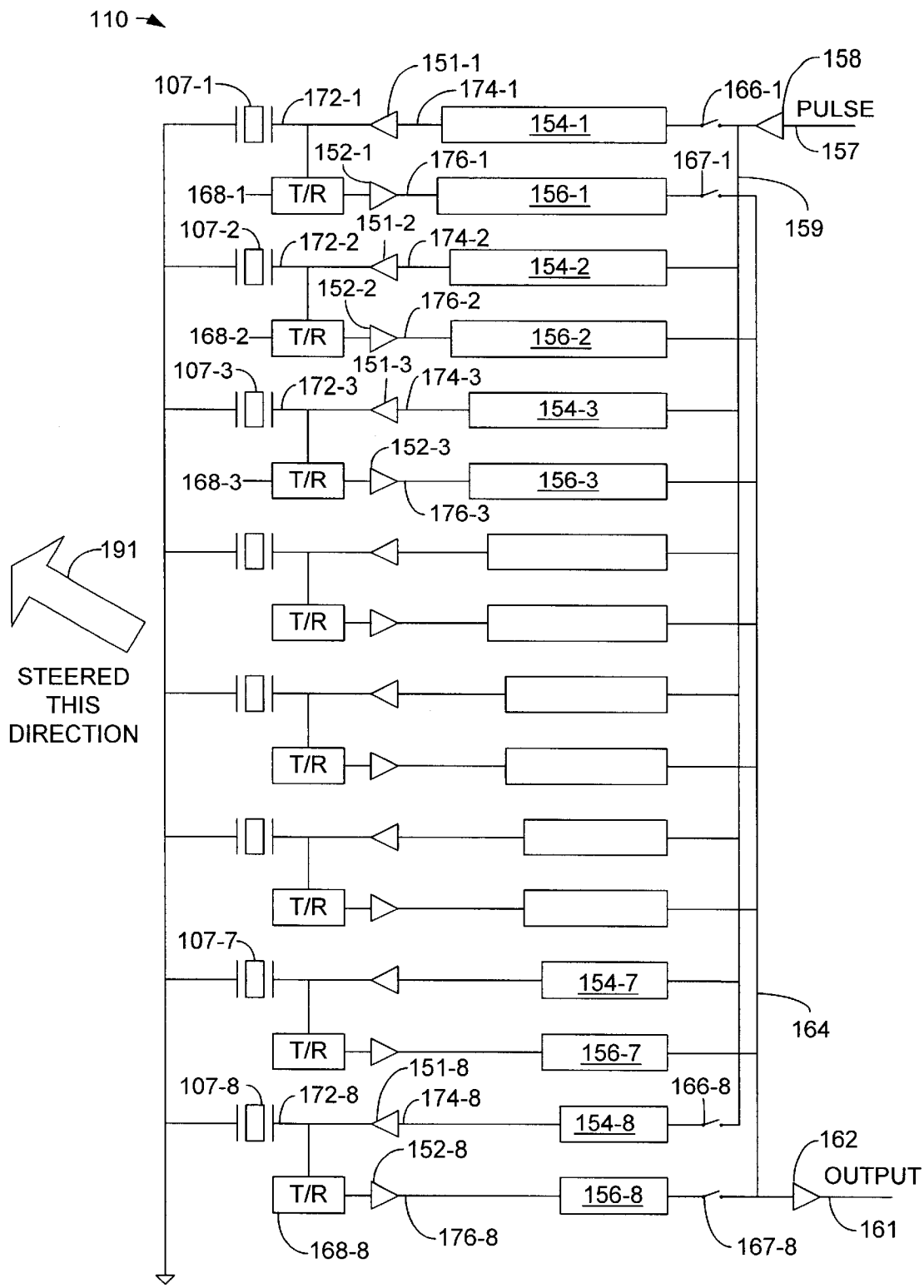
FIG. 4 is a schematic view illustrating the transducer array of FIG. 1A in a steered arrangement opposite that shown in FIG. 3.

FIG. 4 is a schematic view illustrating the transducer array 110 of FIG. 1A steered in the direction indicated by arrow 191. The transducer array 110 illustrated in FIG. 4 is similar to that shown in FIG. 3 with the exception that transmit delay line 154-2 and receive delay line 156-2 are longer in duration than transmit delay line 154-7 and receive delay line 156-7, respectively. As shown in FIG. 4, the transmit delay lines 154-2 through 154-7 and the receive delay lines 156-2 through 156-7 are arranged to cause a delay opposite to that shown in FIG. 3, resulting in a beam steered in the direction indicated by arrow 191. The direction indicated by arrow 191 is also non-perpendicular with respect to that shown in FIG. 2, but is in the opposite direction to that shown with respect to FIG. 3.

Referring again to FIG. 4, in similar fashion to that described with respect to FIG. 3, switches 166-1 and 166-8 for transmit events and switches 167-1 and 167-8 for receive events, are the only switches open, therefore providing a larger transducer aperture than that shown in FIG. 2. The aperture shown in FIG. 4 includes transducer elements 107-2 through 107-7. In this manner, the above-mentioned steering anomalies resulting from steering the transmit and receive beams are compensated by an increase in transducer array aperture.

Figure 5:
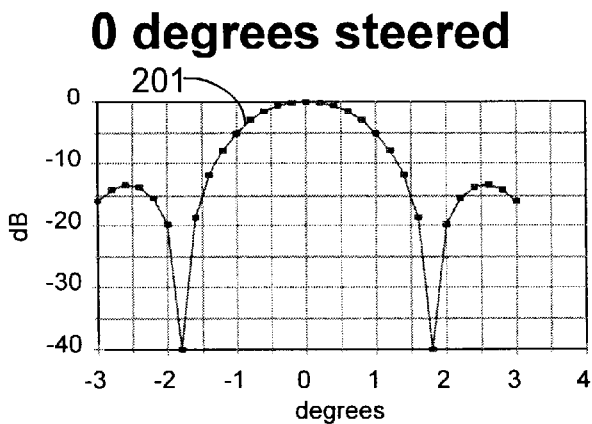
FIG. 5 is a graphical representation of the transducer array of FIG. 2 illustrating the beam plot of a substantially perpendicular beam.

FIG. 5 is a graphical representation of the transducer array 110 of FIG. 2 illustrating the beam plot of a zero degrees steered (substantially perpendicular) beam. The beam plot 201 shown in FIG. 5 corresponds to the transducer array 110 of FIG. 2 having a beam steered in the direction indicated by arrow 171, resulting in the transmission of a substantially perpendicular beam.

Figure 6:
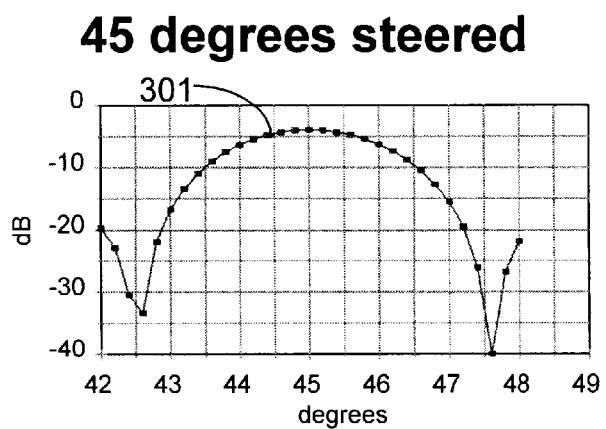
FIG. 6 is a graphical representation illustrating a transmit beam steered forty-five degrees without the benefit of aperture correction.

FIG. 6 is a graphical representation illustrating a transmit beam steered forty-five degrees without the benefit of aperture correction. As shown, beam plot 301 represents a beam that is much wider and lower in amplitude than that shown with respect to FIG. 5, resulting in a beam having reduced power and reduced resolution.

Figure 7:
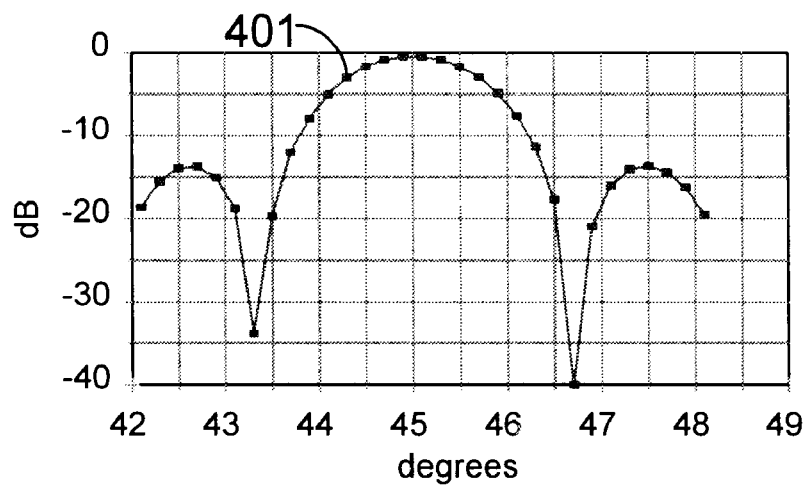
FIG. 7 is a graphical representation illustrating a transmit beam steered forty-five degrees and including a wider aperture compensating for steering anomalies.

FIG. 7 is a graphical representation 400 illustrating a transmit beam 401 steered forty-five degrees and including a wider aperture compensating for steering anomalies.

Beam plot 401 corresponds to the transducer arrays 110 of FIGS. 3 and FIG. 4. As illustrated, beam plot 401, which includes a wider transducer aperture than that shown with respect to FIG. 6, shows a marked improvement in beam quality and compensates for the reduced power and reduced resolution produced by the uncompensated beam of FIG. 6.

It will be apparent to those skilled in the art that many modifications and variations may be made to the preferred embodiments of the present invention, as set forth above, without departing substantially from the principles of the present invention. For example, the present invention can be used in conjunction with any steered ultrasonic transducer array. Furthermore, the concepts of the present invention are applicable at various interrogation and receive frequencies and bandwidths. All such modifications and variations are intended to be included herein within the scope of the present invention, as defined in the claims that follow.

What is claimed is:

1. A method for adjusting a transducer transmit aperture to compensate for transducer steering angle anomalies, the method comprising the steps of:

applying an excitation signal to a first plurality of selected transducer elements in a transducer array, each of said first plurality of selected transducer elements excited at a time relative to the time of excitation of others of said first plurality of selected transducer elements, said excitation signal resulting in a steered ultrasonic beam, and changing the angle of said steered ultrasonic beam without causing steering angle anomalies by varying the relative excitation times of each of a second plurality of selected transducer elements as a function of steering angle.

2. The method of claim 1, wherein the step of compensating comprises:

applying said excitation signal to said different transducer elements where the number of different transducer elements selected for a non-perpendicular steering angle is greater than the number of different transducer elements selected for a substantially perpendicular steering angle.

3. The method of claim 1, wherein the step of compensating comprises:

applying said excitation signal to said different transducer elements where the extent of transducer elements selected for a non-perpendicular steering angle is greater than the extent of transducer elements selected for a substantially perpendicular steering angle.

4. The method of claim 1, wherein said excitation signal is transmitted at a fundamental frequency and received at a harmonic of said fundamental frequency.

5. A method for adjusting transducer receive aperture to compensate for transducer steering angle anomalies, the method comprising the steps of:

receiving acoustic energy in a first plurality of selected transducer elements of a transducer array;

converting, in each of said selected transducer elements, said received acoustic energy into an electrical signal corresponding to said acoustic energy received by each of said first plurality of selected transducer elements;

delaying each electrical signal by a time relative to the delay of the electrical signal for each of said first plurality of selected transducer elements;

summing said received electrical signals corresponding to each of said first plurality of selected transducer elements resulting in a steered receive sensitivity; and changing an angle of said steered sensitivity without causing steering angle anomalies by varying a delay of an electrical signal associated with each of a second plurality of selected transducer elements as a function of steering angle.

6. The method of claim 5, wherein the step of compensating further comprises summing said received electrical signals corresponding to said different transducer elements where the number of different transducer elements selected for a non-perpendicular steering angle is greater than the number of different transducer elements selected for a substantially perpendicular steering angle.

7. The method of claim 5, wherein the step of compensating further comprises summing said received electrical signals corresponding to said different transducer elements where the extent of different transducer elements selected for a non-perpendicular steering angle is greater than the extent of different transducer elements selected for a substantially perpendicular steering angle.

8. The method of claim 5, wherein said received acoustic energy is received at a frequency that is a harmonic of a fundamental frequency.

9. A system for adjusting transducer transmit aperture to compensate for transducer steering angle anomalies, comprising:

a transducer array including transducer elements;

an excitation signal that is applied to a first plurality of selected transducer elements, each of said first plurality of selected transducer elements excited at a time relative to the time of excitation of each others of said first plurality of selected transducer elements, said excitation signal resulting in a steered ultrasonic beam; and a plurality of delay elements and associated switches configured to change the angle of said steered ultrasonic beam without causing steering angle anomalies by varying the relative excitation times of each of a second plurality of selected transducer elements as a function of steering angle.

10. The system of claim 9, wherein said transducer elements are lead zirconate titanate (PZT) elements.

11. The system of claim 9, wherein said transducer elements are micro-machined ultrasonic transducer (MUT) elements.

12. The system of claim 9, wherein said transducer array is a one-dimensional array.

13. The system of claim 9, wherein said transducer array is a two dimensional array.

14. The system of claim 9, wherein said excitation signal is transmitted at a fundamental frequency and received at a harmonic of said fundamental frequency.

15. A computer readable medium having a program for adjusting a transducer transmit aperture to compensate for transducer steering angle anomalies, the program comprising:

logic configured to apply an excitation signal to a first plurality of selected transducer elements in a transducer array, each of said first plurality of selected transducer elements excited at a time relative to the time of excitation of others of said first plurality of selected transducer elements, said excitation signal resulting in a steered ultrasonic beam; and logic configured to change the angle of said steered ultrasonic beam without causing steering angle anomalies by varying the relative excitation times of each of a second plurality of selected transducer elements as a function of steering angle.

16. The program of claim 15, wherein the logic configured to compensate comprises applying said excitation signal to said different transducer elements where the number of different transducer elements selected for a non-perpendicular steering angle is greater than the number of different transducer elements selected for a substantially perpendicular steering angle.

17. The program of claim 15, wherein the logic configured to compensate comprises applying said excitation signal to said different transducer elements where the extent of said different transducer elements selected for a non-perpendicular steering angle is greater than the extent of different transducer elements selected for a substantially perpendicular steering angle.

18. The program of claim 15, wherein said excitation signal is transmitted at a fundamental frequency and received at a harmonic of said fundamental frequency.

* * * * *